United States Patent
Harth et al.

(10) Patent No.: US 6,835,202 B2
(45) Date of Patent: Dec. 28, 2004

(54) APPARATUS AND METHOD FOR HIGH ENERGY PHOTODYNAMIC THERAPY OF ACNE VULGARIS AND SEBORRHEA

(75) Inventors: Yoram Harth, Haifa (IL); Avner Korman, Herzlia (IL)

(73) Assignee: Curelight Ltd., Or-Akiva (IL)

(*) Notice: Subject to any disclaimer, the term of this patent is extended or adjusted under 35 U.S.C. 154(b) by 199 days.

(21) Appl. No.: 09/756,130

(22) Filed: Jan. 9, 2001

(65) Prior Publication Data

US 2001/0023363 A1 Sep. 20, 2001

Related U.S. Application Data

(63) Continuation-in-part of application No. PCT/IL99/00374, filed on Jul. 7, 1999.
(60) Provisional application No. 60/092,225, filed on Jul. 9, 1998.

(51) Int. Cl.[7] ................................................ A61N 5/06
(52) U.S. Cl. .......................... 607/91; 607/90; 128/898; 606/9
(58) Field of Search .................... 606/9; 607/88–94; 128/898

(56) References Cited

U.S. PATENT DOCUMENTS

| | | | |
|---|---|---|---|
| 2,183,726 A | * 12/1939 | Sommer et al. ............. 222/281 |
| 4,229,658 A | * 10/1980 | Gonser .................... 250/493.1 |
| 4,407,282 A | 10/1983 | Swartz |
| 4,790,500 A | * 12/1988 | Mori ........................... 248/49 |
| 4,930,504 A | 6/1990 | Diamantopoulos et al. |
| 5,259,380 A | * 11/1993 | Mendes et al. ............. 607/115 |
| 5,549,660 A | 8/1996 | Mendes et al. |
| 5,576,013 A | * 11/1996 | Williams et al. ............ 424/423 |
| 5,591,219 A | * 1/1997 | Dungan .................. 250/504 H |
| 5,620,478 A | * 4/1997 | Eckhouse .................... 607/88 |
| 5,634,711 A | * 6/1997 | Kennedy et al. ............ 362/119 |
| 5,707,401 A | 1/1998 | Talmore |
| 5,707,403 A | 1/1998 | Grove et al. |
| 5,736,582 A | 4/1998 | Devillez |
| 5,817,089 A | 10/1998 | Tankovich et al. |

(List continued on next page.)

FOREIGN PATENT DOCUMENTS

| | | |
|---|---|---|
| EP | 0 105 584 | 4/1984 |
| GB | 2 272 278 | 5/1994 |
| WO | WO 95/16454 | 6/1995 |

OTHER PUBLICATIONS

Meffert et al., Dermatol–Monattschr. 1990; 176 (10): 597–603.
Sigurdsson et al., Dermatology 1997; 94:256–260.
Sigurdsson V, et al., "Pharmacology and Treatment. Phototherapy of Acne Vulgaris with Visible Light", Dermatology, vol. 194, No. 3, 1997, pp. 256–260.

*Primary Examiner*—Lee Cohen
*Assistant Examiner*—Henry M Johnson, III

(57) ABSTRACT

An apparatus and method for the phototherapy of different skin conditions, particularly acne vulgaris and seborrhea. The invention consists of a combined treatment with violet/blue light source with a spectral emission in the range of 405–440 nanometer and possible additional spectral bands in the green and red part of the spectrum and the topical application of oxygen transporting compounds, and/or a methylene blue solution. The apparatus includes at least one narrow spectral band light source with spectral emittance concentrated in the violet/blue spectral band and an optical system for controlling spectra and beam parameters of said light source and a mechanical fixture for holding the said light source at an adjustable distance and direction related to the skin treated area, and an electronic unit to control the duration and power and spectral bands of the emitted radiation.

44 Claims, 13 Drawing Sheets

U.S. PATENT DOCUMENTS

| | | | | |
|---|---|---|---|---|
| 5,836,999 A | * | 11/1998 | Eckhouse et al. | 607/88 |
| 5,843,143 A | * | 12/1998 | Whitehurst | 424/423 |
| 5,879,376 A | | 3/1999 | Miller | |
| 5,896,457 A | * | 4/1999 | Tyrrel | 381/56 |
| 6,165,170 A | * | 12/2000 | Wynne et al. | 606/9 |
| 6,183,500 B1 | * | 2/2001 | Kohler | 607/88 |
| 6,223,071 B1 | * | 4/2001 | Lundahl et al. | 600/476 |
| 6,235,016 B1 | * | 5/2001 | Stewart | 606/13 |
| 6,269,818 B1 | * | 8/2001 | Lui et al. | 128/898 |
| 6,324,418 B1 | * | 11/2001 | Crowley et al. | 600/179 |
| 2003/0032950 A1 | * | 2/2003 | Altshuler et al. | 606/9 |

\* cited by examiner

APPARATUS AND METHOD FOR HIGH ENERGY PHOTODYNAMIC THERAPY OF ACNE VULGARIS AND SEBORRHEA

RELATED APPLICATIONS

This application is a continuation in part application of PCT Application No. PCT/IL99/00374, filed Jul. 7, 1999 and claims benefit of Provision 60/092,225 filed Jul. 9, 1998.

FIELD AND BACKGROUND OF THE INVENTION

The present invention relates to an apparatus and method for the photodynamic therapy treatment of acne vulgaris and seborrhea and, more particularly, to a violet/blue light radiating system that illuminates a collimated narrow bandwidth beam on the treated skin area. The method relates to the combined photodynamic skin treatment including narrow band violet/blue light radiation and topical application of oxidative and/or keratolytic agents.

The enlargement and obstruction of sebaceous glands cause acne vulgaris. Due to the accumulation of sebum in the glands, bacteria, mainly *propionibacterium acnes* (*p. acnes*), proliferate in the glands. These bacteria cause inflammation and later the formation of pustular lesions and acne cysts, which heal by scarring.

It is known that *p. acnes* produce porphyrins. It is also known that visible light in the violet/blue (405–410 nanometer range), or less efficiently, red (630–670 nanometer range) are able to induce a photodynamic effect in which the porphyrins in the enlarged sebaceous glands react with oxygen to form peroxides. These peroxides are short-lived toxic compounds that are able to eliminate, or considerably diminish, the number of bacteria in the glands.

Photodynamic therapy (PDT) is based on the optimal interaction of four elements; light, photosensitizer, oxygen and skin penetration. Prior patents and publications related to acne phototherapy dealt only with the first two elements of PDT, i.e., and light exposure and sebaceous gland porphyrins. Studies have shown that the photodestruction of *p. acnes* is increased exponentially in an oxygen rich environment.

Various attempts have been made to treat acne with light; Mendes et al. (U.S. Pat. No. 5,549,660) described a method for the light therapy of acne using low intensity red light. Their apparatus was meant to treat acne through it effect on macrophages in the skin. Its low light intensity is not sufficient for an efficient photodynamic destruction of *p. acnes* in the deeper layers of the skin, High intensity visible light phototherapy for acne was described by Meffert et al, (Dermatol-Monatsschr. 1990; 176(10): 597–603) but they used a light source emitting not only visible light but also UVA comprising up to 15–20% of the total irradiation dose. Sigurdsson et al (Dermatology 1997; 94:256–260), used Philips HPM-10 400 W combined with an UVILEX 390-filter (Desag. Germany) that filters most but not all ultraviolet A (UVA) harmful rays. The spectrum of their lamp peaked at 420 nanometer and had 2 other small peak of emission at 405 and 435 nanometer. Their apparatus emitted at 40 cm; 0.5 $J/cm^2$ of UVA, 20 $Jcm^2$/of violet/blue and 5 $J/cm^2$ of green light.

SUMMARY OF THE INVENTION

Basic science research has shown in vitro that the viability of *p. acnes* relates inversely to light intensity and to oxygen levels to which the *p. acnes* are exposed. Sigurdsson et al achieved with their apparatus 30% reduction of the total severity of acne and particularly 49% reduction of the number of pustules. The rate of success can be drastically improved by adding and penetrating oxygen to the skin daily and/or immediately before skin exposure to high intensity violet/blue light According to the present invention there is provided an apparatus and a method for acne phototherapy, achieved by the use of a specially designed apparatus having a narrow spectral band violet/blue light emission with a possible additional spectral line, combined with a pre-treatment application on the treated skin area of an oxygen transporting compounds, based on the use of one or more of the materials from the group of compounds consisting of perfluorocarbons, oxidative substances, keratolytic substances and external photosensitizer such as methylene blue 0.1–5%.

There is thus provided, in accordance with an embodiment of the present invention, apparatus for treatment of a skin disorder. The apparatus includes at least one light source with spectral emittance concentrated in at least one specific narrow spectral band, wherein one spectral band is in the range of 405 to 440 nm, an optical system for collecting and shaping light emitted from the at least one light source and an electronic unit to control parameters associated with the spectral emittance from the at least one light source.

Furthermore, in accordance with an embodiment of the present invention, the parameters include at least one of a group including duration, power and emitted spectral bands of the light source emittance.

Furthermore, in accordance with an embodiment of the present invention, the apparatus further includes a mechanical fixture for holding the light source at an adjustable distance and direction related to a treatment area.

Furthermore, in accordance with an embodiment of the present invention, the illumination energy of the light source flux, is higher than a predetermined threshold level. The threshold level is a level required for biological destruction of acne and seborrhea causing factors.

Furthermore, in accordance with an embodiment of the present invention, the illumination energy threshold level of the illumination light source is at least 40 mw/cm2 at a distance from the light source of 30 cm.

Furthermore, in accordance with an embodiment of the present invention, the illuminated area on a patient body includes an illumination area large enough to illuminate an infected typical size skin area from a fixed position of the light source related to the skin area, In accordance with an embodiment of the present invention The illuminated area is at least 400 cm2.

Additionally, in accordance with an embodiment of the present invention, the apparatus further includes an illumination head having at least two converging collimated beams from at least two directions, each of the beams generated by a separate light source positioned at a distance from the other at least one light source.

Additionally, in accordance with an embodiment of the present invention, the apparatus further includes a computer controlled imaging unit for imaging an illuminated treated area and for monitoring by counting lesions on the treated area, using computerized counting techniques.

Additionally, in accordance with an embodiment of the present invention, the apparatus further includes a computer controlled display unit for displaying the imaged illumination treated area, wherein counting is carried out by an operator marking lesions on the display of the illumination treated imaged surface area. Alternatively, the computer lesions counting by image processing techniques to detect and count each lesion in the illumination treated imaged surface area. The score of the computer lesion counting is recorded in a computer memory to enable monitoring the lesion healing process through a series of consecutive treatments.

Furthermore, in accordance with an embodiment of the present invention, the computer controlled imaging unit idisplay image includes at least one of a group includes a graph of the number of counted lesions versus accumulated treatment time and a table consisting of number of counted lesions in each treatment session.

Furthermore, in accordance with an embodiment of the present invention, the apparatus further includes at least one optical element of a group includes a liquid filled light guide, a solid transparent light guide, a fiber bundle light guide and an array of lenses and mirrors for collecting and conducting the light source radiation and illuminating the skin treated area at an adjustable distance, energy density and direction.

Furthermore, in accordance with an embodiment of the present invention, the light source is a Gallium, Mercury and halides gas mixture discharge lamp with peak emission in the 405–440 spectral band. Alternatively, the light source is selected from the group including Ion Krypton gas laser with a spectral emission in the range 405 to 440 nm, and a diode. The diode is selected from the group consisting of violet/blue laser diodes, and light emitting diodes (LED) with narrow spectral band emission in the range 405–440 nm.

Furthermore, in accordance with an embodiment of the present invention, the light is collected and projected by at least one reflector, wherein the reflector is selected from the group includes of an elliptical cross-section cylindrical reflector, parabolic cross-section cylindrical reflector, and an asymmetric aspheric reflector.

Alternatively, the light is collected and further collimated by a set of two orthogonal cylindrical lenses.

Furthermore, in accordance with an embodiment of the present invention, the light of the at least one light source is collected by an elliptical cross-section reflector having a first focal point and a second focal point. The light source is disposed at the first focal point and has disposed at the second focal point a slit shape aperture of a slit to circular beam shaping and conducting light guide.

Additionally, according to the present invention there is also provided a method of treating a skin disorder. The method includes providing a light radiation source having spectral characteristics of at least one of a group of narrow spectral bands consisting of violet/blue (405–440 nm), red (630–670 nm) and green (520–550 nm) light, applying a compound to a skin area, illuminating the skin area with the light radiation source, and additionally illuminating the skin area after a predetermined time period.

Furthermore, in accordance with an embodiment of the present invention, the skin disorder is one of a group including acne and seborrhea.

Furthermore, in accordance with an embodiment of the present invention, the compound is selected from a group consisting of a topical oxygen transporting perfluoroocarbon, an oxidative agent, a keratolytic agent and a methylene blue solution Furthermore, in accordance with an embodiment of the present invention, the predetermined time period is at least 24 hours.

Furthermore, in accordance with an embodiment of the present invention, the method further includes a pretreating application of the compound, concentrating the light on the skin area by an optical system and a mechanical fixture, and exposing the skin area at specific time intervals.

Furthermore, in accordance with an embodiment of the present invention, the time interval is 1–5 weekly exposure to violet/blue light for typically 2–10 weeks, with a minimum 24 hour's time gap between exposures.

Furthermore, in accordance with an embodiment of the present invention, the step of illuminating is accomplished by projecting on the skin area with an illumination power in the range of 10 mW/cm$^2$ to 500 mW/cm$^2$ of violet/blue light radiation.

Furthermore, in accordance with an embodiment of the present invention, the compound is hydrogen peroxide in the concentration of 1–10% by weight and the concentration of salicylic acid is 1–10% by weight.

Furthermore, in accordance with an embodiment of the present invention, pretreating is carried out daily or alternatively immediately before light exposure.

Furthermore, in accordance with an embodiment of the present invention, the material is selected from the group consisting of oxidative and keratolytic compounds is in an aqueous gel. Alternatively, the material selected from the group consisting of oxidative and keratolytic compounds is in oil in water emulsion.

Furthermore, in accordance with an embodiment of the present invention, the oxidative and/or keratolytic compound is within a material selected from the group consisting of a liposome and a positively charged submicron emulsion. Alternatively, the oxidative and/or keratolytic compounds is in a Propylene glycol 10–50% base or an oil in water emulsion mixed with molecular oxygen that is sprayed continuously on the skin before or during light exposure.

Furthermore, in accordance with an embodiment of the present invention, methylene blue 0.1–5% in distilled water or gel bases is applied to the skin before or during light exposure.

It provides a way to increase the photodestruction of p. acnes by providing and illuminating the affected area with high intensity monochromatic, or multi-spectral discrete emission lines light energy, exactly matching the optimal action spectrum of the photosensitizer created by the p. acnes.

Methylene blue is a dye used parentally for treatment of methemoglobinemia in newborns and topically for disinfecting of skin. In vitro and in vivo studies have shown that Methylene blue may be activated by light to induce a photodynamic reaction. Methylene blue was used for the inactivation of herpes virus helicoabacter pillory and for the experimental therapy of skin bladder and esophageal cancers. The method of photodynamic therapy may also be enhanced by adding an external photosensitizing agent such as methylene blue in a concentration of 0.1–5%.

The proposed method significantly increases the oxygen pressure in the sebaceous glands through the use of oxygen transporting compounds based on perfluorocarbons and/or oxidative emulsions. The proposed method also enhances light and compound penetration into the skin using translucent gels and keratolytic agents. The proposed apparatus emits light energy above a biologic bacteria destruction threshold. The light source generates a high intensity non-coherent light in the exact narrow spectral band or bands, needed for the activation of the photodynamic reaction while filtering out the harmful UV light. This narrow and specific wavelength range radiation enables the administration of sufficient intensity of light to the deeper layers of the dermis without excessive heat formation in the epidermis. The required spectral band is emitted by the present invention light source for the photodynamic destruction of *p. acnes* in the acne sebaceous glands.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is an apparatus, which can be used for photodynamic treatments in phototherapy. Specifically, the present invention can be used for the non-invasive treatment of acne vulgaris and seborrhea, thereby enabling treating various parts of the patients body with ability to control the illumination power, energy spatial distribution, exposure duration and illumination source emittance spectral bands.

The principles and operation of the apparatus for phototherapy treatment according to the present invention may be better understood with reference to the drawings and the accompanying description.

Figure 1:
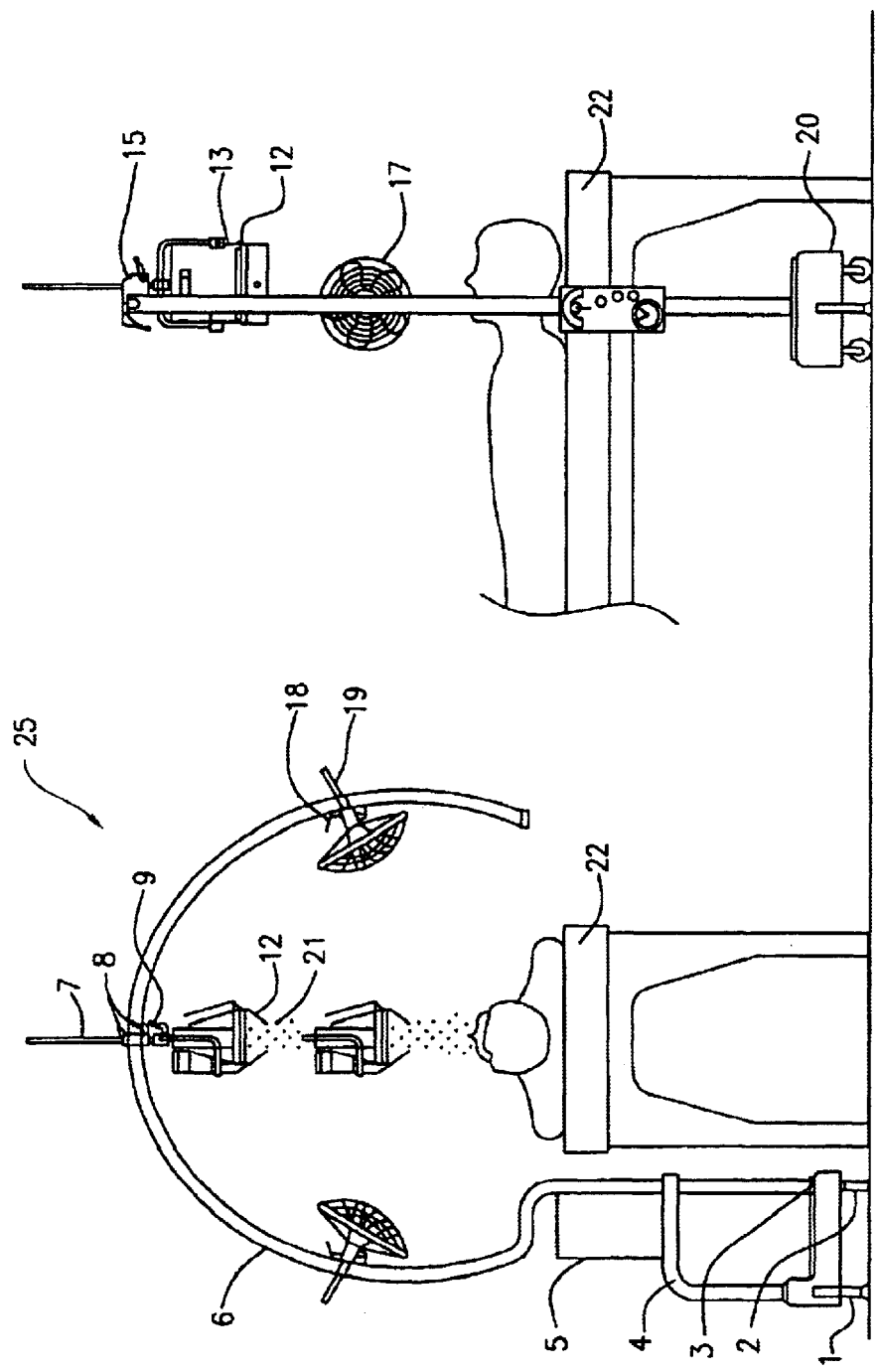
FIG. 1 is a schematic front and side view illustrations of one embodiment of the photodynamic treatment apparatus according to the present invention.

Referring now to the drawings, FIG. 1 is a schematic front and side view illustration of the photodynamic treatment apparatus according to the present invention, which is referred to herein below as system 25.

System 25 includes a violet/blue light source fixture 13, which can be moved repositioned and directed to the treated patient specific skin area by adjustment unit 15. It can also be lifted up or lowered down in order to change the effective radiated energy flux on the treated area, by using pole unit 7 and handle 8. The apparatus light source is mounted on a mechanical arc shaped fixture 6 for holding and supporting the light source at an adjustable distance and direction relative to the patient's treated skin area. The apparatus mechanical fixture 9 allows horizontal, vertical and radial placement and directing of light beam 21 from the light unit 13 to the patient's treated part of the body.

Unit 17 is a schematic presentation of an air blower or a fan that serves to cool and remove access heat from the treated skin area. Units 18 and 19 are mechanisms to adjust the required position of unit 17.

Unit 5 is a control board for the apparatus enabling control of amp power, illumination duration, air cooling operational parameters and general on/off and mains control functions.

Units 4 and 20 are a structural element and a balancing weight to stabilize the apparatus in a vertical up-right position. Unit 3 is a mechanical axis around which the entire apparatus arc shaped structure 6 can be rotated and refitted in any required horizontal angular position related to the treated patient bed 22.

Wheel 2 and pole 1 are elements required to move and refit the position of the apparatus according to the operational needs of the system operator.

Light source fixture 13 of consists of a lamp or a laser light source that emits violet/blue light with a peak at 405–420 nm. Close to a hundred percent of the light source ultra violet/blue light (UV) is filtered out by an integrated optical system. The required narrow spectral emission band of violet/blue light source is radiated by the present patent dedicated arc lamp due to a special gas mixture as described below, within the lamp, or by a gas laser source, or by a violet/blue light emitting semiconductor diode junction. The above light sources in a single source type embodiment, or in a combination of two or three type of light sources, allows optimal violet/blue light radiation with or without additional narrow spectral band lines in the red or green parts of the spectrum. The present invention light source enables the minimization of heat production at the treated target to a max of 23 degrees Celsius on the epidermis at 30–40 cm. A mechanical shutter 12 in front of the light source 13 may be used to exactly define the treated area.

Figure 2B:
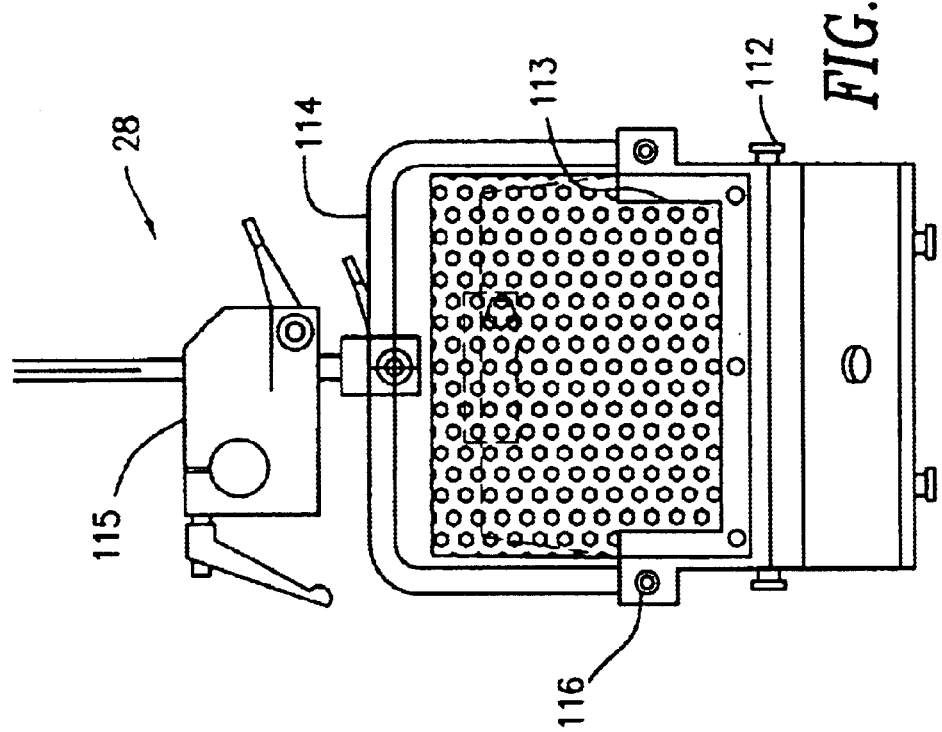
FIGS. 2A and 2B are schematic side view and front view illustrations respectively of the illumination head unit, the same embodiment of the present invention apparatus wherein the illumination unit head structure is based on a violet/blue light source of a gas discharge lamp.
Figure 2A:
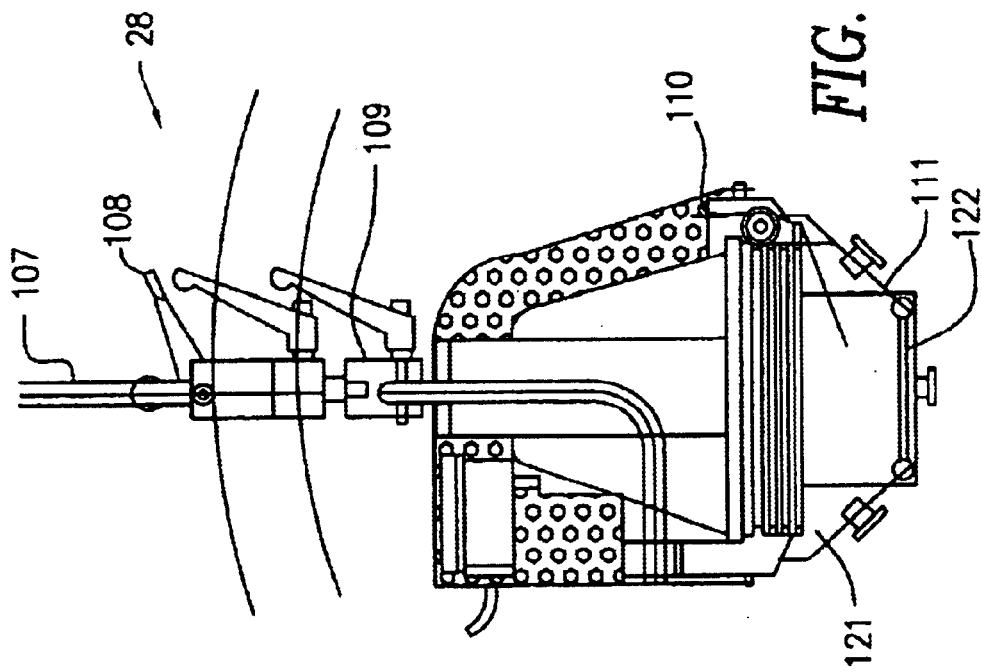

FIGS. 2A and 2B are schematic side and front view illustrations of the illumination head unit 13 according to the present invention, referred to herein below as system 28.

Illumination system 28 includes a filter unit 121 for filtering out the radiated energy spectral part, which is out of the preferred specific bandwidth in the violet/blue and/or the red spectrum, as previously described in the above background paragraph of the invention. Unit 111 is a set of four mechanical flaps with a control knob 112 and a pivoting axis 110 that create together an adjustable aperture iris unit to control the size and collimation parameters of system 28 radiated light beam, U shaped arm 114 holds and supports the illumination unit housing 113. Unit 109 enables rotation of the system 28 around vertical pivot axis 107 and to lock it in the preferred rotational angle. Unit 115 enables changing position by sliding and further fixing in a preferred position system 28 along the apparatus support arc 106. Unit 115 also enables sliding system 28 up or down and then fixing its position Unit 122 is an optional mechanical support housing and a lens for focusing and concentrating the system 28 illumination beam on a smaller area of the treated skin, thus creating a higher light energy flux whenever required for a specific treatment.

Figure 3A:
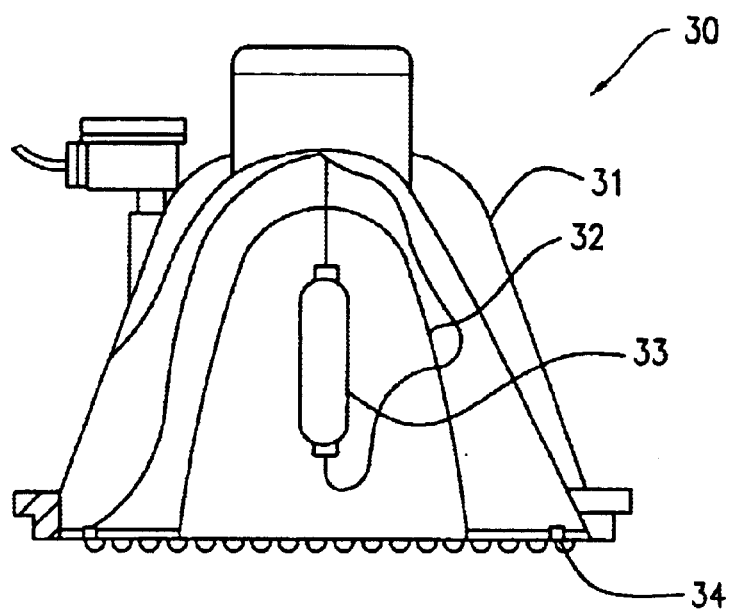
FIGS. 3A and 3B are schematic top and bottom views respectively of the light source unit in the apparatus of FIG. 1, in an embodiment wherein the illumination unit structure is based on a circular array of LED's, or laser diodes, emitting a narrow spectral band red light illumination component, the array is integrated on the perimeter of a parabolic cross-section reflector, in the focal point of which is situated a high illumination intensity, narrow spectral band, violet/blue light gas discharge light source.
Figure 3B:
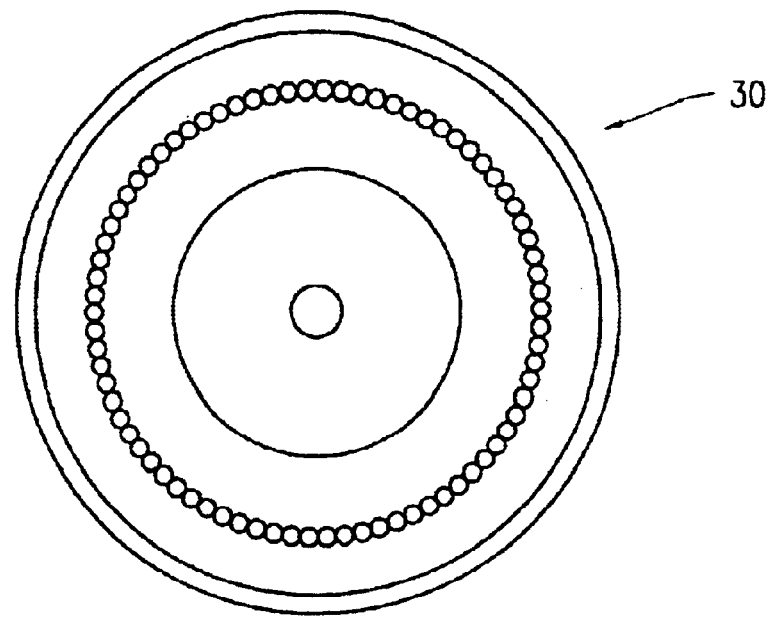

FIGS. 3A and 3B are schematic top and bottom views of another preferred embodiment of the present invention lighting head unit 13 of the apparatus described in FIG. 1, referred to herein below as system 30.

System 30 includes a housing unit 31 and a reflector 32 having preferably a parabolic vertical cross section. The gas discharge lamp 33 is assembled into reflector unit 32 in a way that fixes the center of the lamp illumination arc in the focal point of the reflector. Lamp 33 is a specially designed Gallium and Lead halides gas mixture discharge lamp with peak emission in the 405–430 spectral band.

Unit 34 is a circular array of red emission LED's or red light laser diodes installed around the aperture perimeter of the reflector unit 33.

Figure 4:
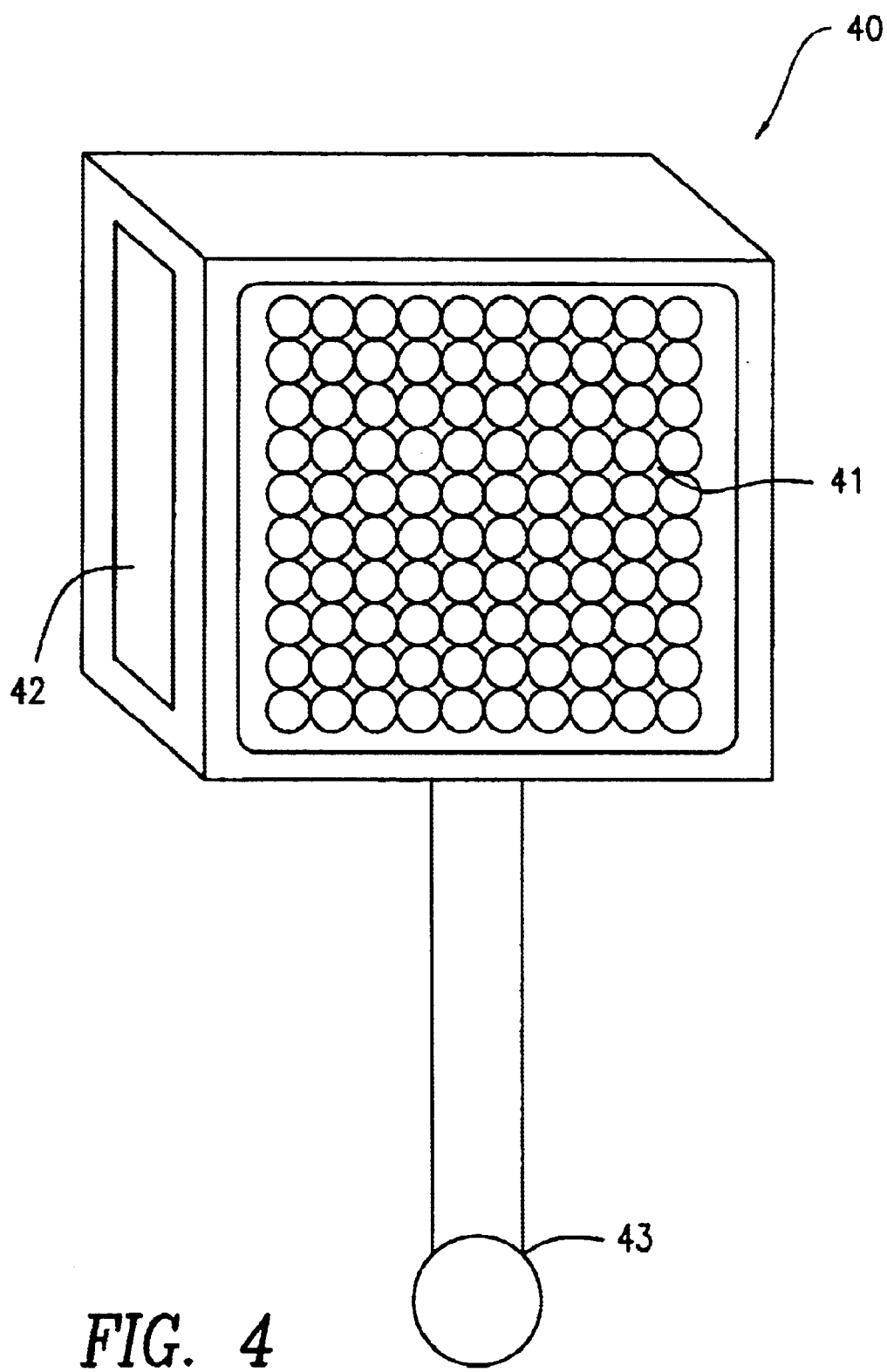
FIG. 4 is a schematic bottom view illustration of the present invention violet/blue light source, in another embodiment, wherein the illumination unit structure is based on a two dimensional array of LED's, or laser diodes, emitting a preferred narrow spectral band violet/blue light illumination component, the two dimensional array can also include any spatial distribution combination of violet/blue narrow spectral band emitting laser diodes or LED's, together with red light LED's, or laser diodes emitting in the preferred red spectral band.

FIG. 4 is a schematic illustration of another preferred embodiment of the present invention lighting head unit 13 of the apparatus described in FIG. 1, referred to herein below as system 40.

System 40 includes a housing unit 42 and a two-dimensional array of LED's, or laser diodes 41, emitting a narrow spectral band violet/blue light illumination component. These semiconductor solid state light sources can be GaN or ZnSe components. The two-dimensional array can also include narrow spectral band red light LED's, or laser diodes, emitting in the preferred red spectral band. Unit 43 is a mechanical structure for attaching system 40 to the apparatus of FIG. 1.

Figure 5:
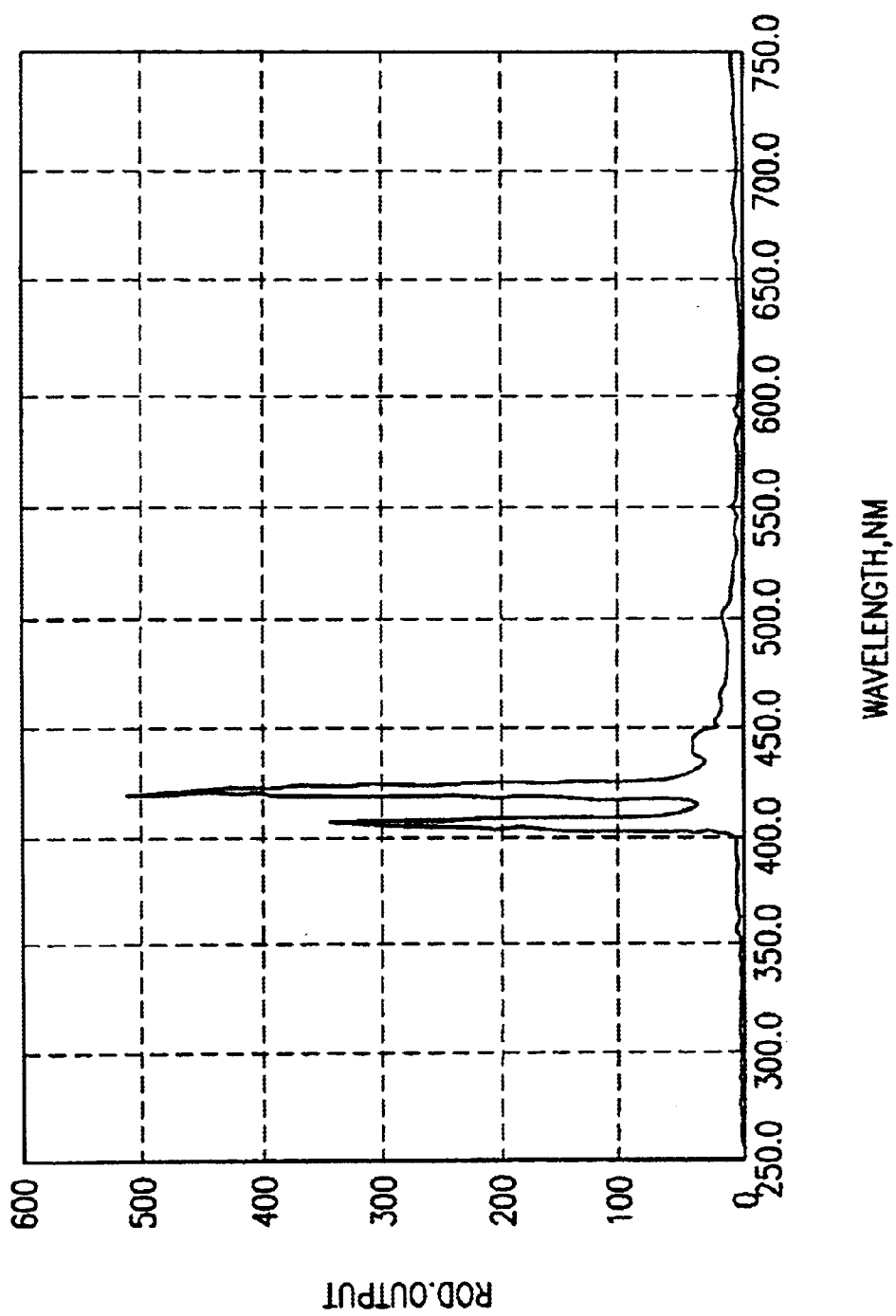
FIG. 5 illustrates a typical spectral distribution of the light energy emitted by the present invention dedicated violet/blue light source, in the embodiments wherein the light source is a gas discharge lamp.

FIG. 5 illustrates a typical spectral distribution of the light energy emitted by the present invention dedicated violet/blue gas discharge lamp based light source, before further spectral optical filtration is done, in the embodiments wherein the light source is a gas discharge lamp.

Figure 6A:
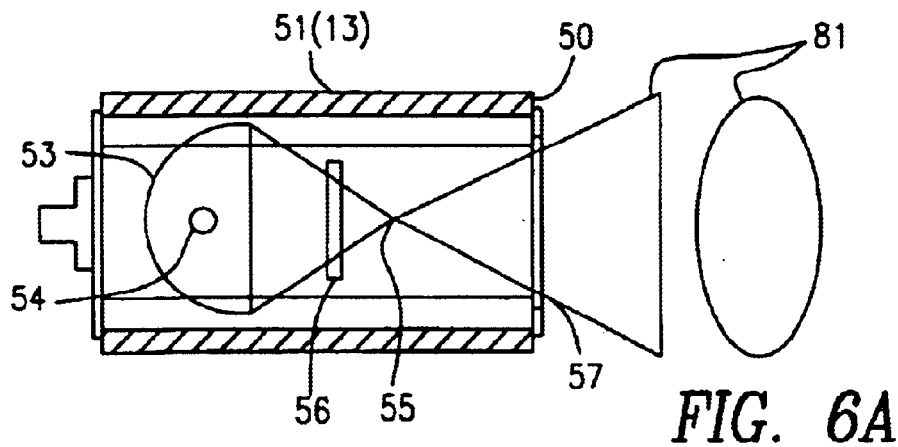
FIGS. 6A–6C illustrate another set of an additional three preferred embodiments of the illumination head in the apparatus according to the present invention, wherein all these embodiments are based on the application of a single axis elliptical cross-section cylindrical reflector, in the first focal point of which is fitted the illuminating gas discharge lamp arc. The image of the gas discharge light source arc is created in the second focal point of the elliptical reflector and can be then directly used for object illumination, or collected and further conducted by a fiber optic slit to circular beam shaping bundle, or collected and reshaped by a dedicated set of two orthogonal cylindrical lenses, to optimally conduct and collimate the light energy on the patients treated skin areas.

FIG. 6A is a schematic cross section illustration of one of a set of three possible preferred embodiments of the present invention lighting head unit 13 of the apparatus described m figure 1, the first possible embodiment is referred to herein below as system 50. Light source head embodiment of system 50 consists of a housing 51 that supports an arc lamp, or a line beam shape laser light source (not shown) that emits violet/blue light with a peak at 405–440 nm. The light source is fixed in the first focal point 54 of an elliptical cross section shape reflector 53. The energy emitted out of the preferred spectral band reflected by the elliptical shaped reflector and is imaged as a line source at its second focal point 55. From the secondary focal point the beam is diverging at a small angle and creates an oval shaped illumination area 81 of typical size 20×10 cm$^2$. at a convenient treatment distance of 30–40 cm. from the lamp housing exit aperture. The non violet spectral part of the light source emission is rejected and filtered out by filter unit 56 and the lamp housing is sealed by tempered glass window 57 possibly coated with a heat mirror layer for the protection of the patient against heat and explosion. The required narrow spectral emission band of violet/blue light source is radiated by the present invention dedicated arc lamp due to a special gas mixture within the lamp, or by a violet/blue light emitting semiconductor diode junction array. The above light sources in a single source type embodiment, or in a combination of two or three type of different spectral emission bands light sources alternative embodiment, allows optimal violet/blue light radiation with, or without, additional narrow spectral band lines in the red or green parts of the spectrum.

Figure 6B:
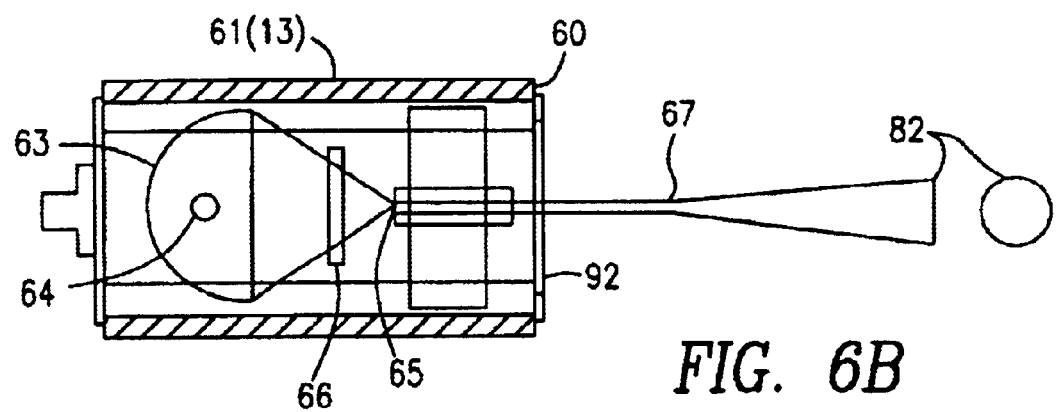

FIG. 6B is a schematic cross section illustration of a second possible preferred embodiment of the present invention lighting head unit 13 of the apparatus described in FIG. 1, the second possible embodiment is referred to herein below as system 60. Light source head embodiment of system 60 consists of a housing 61 that supports an arc lamp, or a line beam shape laser light source (not shown) that emits violet/blue light with a peak at 405–440 nm. The light source is fixed in the first focal point 64 of an elliptical cross section shape reflector 63. The energy emitted out of the preferred spectral band reflected by the elliptical shaped reflector and is imaged as a line source at its second focal point 65. In the secondary focal point 65 the beam enters a slit shape fiber bundle aperture, matching the size and shape of the imaged light line. At the exit circular aperture 67 of this fiber bundle the emerging light is diverging at a typical 40 degrees angle and creates a circular shaped illumination area while its size and consequently the illumination power density can be controlled by changing the distance from the exit fiber end 67 to the patient treated skin area. The UV on violet spectral part of the light source emission is rejected and filtered out by filter unit 66 and the lamp housing is sealed by a cover window 92. The above light sources in a single source type embodiment, or in a combination of two or three type of different spectral emission bands light sources alternative embodiment, allows optimal violet/blue light radiation with, or without additional narrow spectral band lines in the red or green parts of the spectrum.

Figure 6C:
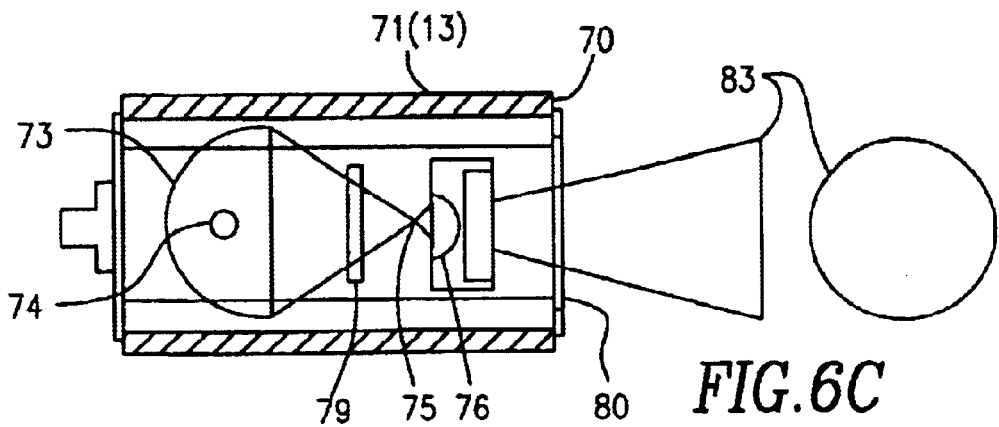

FIG. 6C is a schematic cross section illustration of a third possible preferred embodiment of the present invention lighting head unit 13 of the apparatus described in FIG. 1, the third possible embodiment is referred to herein below as system 70. Light source head embodiment of system 70 consists of a housing 71 that supports an arc lamp, or a line beam shape laser light source (not shown) that emits violet/blue light with a peak at 405–440 nm. The light source is fixed in the first focal point 74 of an elliptical cross section shape reflector 73. The energy emitted out of the preferred spectral band reflected by the elliptical shaped reflector and is imaged as a line source at its second focal point 75. After passing through in the secondary focal point 75 the beam is entering a set of two cylindrical lenses 76 and, which are orthogonal oriented with respect to their linear axis. At the exit of this lens system aperture a close to a circular light illumination area is created of typical size 20×20 $cm^2$. at a convenient treatment distance of 30–40 cm. from the lamp housing exit aperture. The non violet spectral part of the light source emission is rejected and filtered out by filter unit 79 and the lamp housing is sealed by a cover window 80. The above light sources in a single source type embodiment, or in a combination of two or three type of different spectral emission bands light sources alternative embodiment, allows optimal violet/blue light radiation with, or without additional narrow spectral band lines in the red or green parts of the spectrum.

The method according to the present invention improves the results by adding oxygen transporting compounds based on perfluorocarbons and/or oxidative and/or keratolytic agent, daily and or immediately pretreatment. The proposed oxygen transporting agents i.e., perfluorocarbons lipophilic emulsion, release nascent oxygen directly into the sebaceous glands achieving a 76% $O_2$ environment as compared to the atmospheric 20%. The proposed oxidative agents i.e., emulsion or gel of $H_2O_2$ 1–10%, release by contact with the enzyme cathalase present in the skin nascent oxygen. The specific formulations of the emulsion or gel prevent the upward release of the oxygen and cause a short temporary inward pressure of up to 15 Atm. of $O_2$, penetrating to the sebaceous glands situated in the deeper layers of the skin.

The oxygenation of the skin during the phototherapy process raises the efficiency of the desired photodestruction of *p. acnes* and thus decreases of acne lesion number and severity. Added keratolytic agent (i.e. 1–5% salicylic acid) to the applied formulation will enhance diffusion of $O_2$ into the sebaceous glands. Cooling of the applied emulsion or gel minimizes the heat in the epidermis thus allowing a further increase of the light intensity in the sebaceous glands.

Figure 8A:
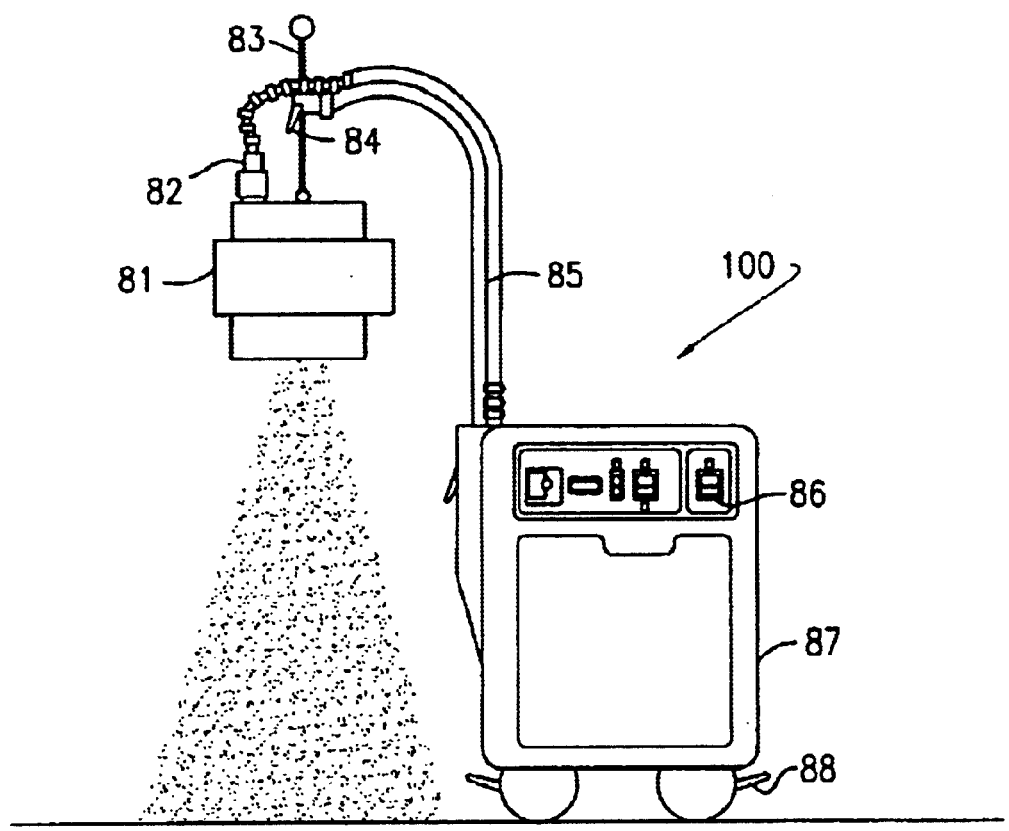
FIGS. 8A and 8B are two schematic views illustrations of another embodiment the present invention light source apparatus, wherein in FIG. 8A the illumination source is operated through a single illumination head.
Figure 8B:
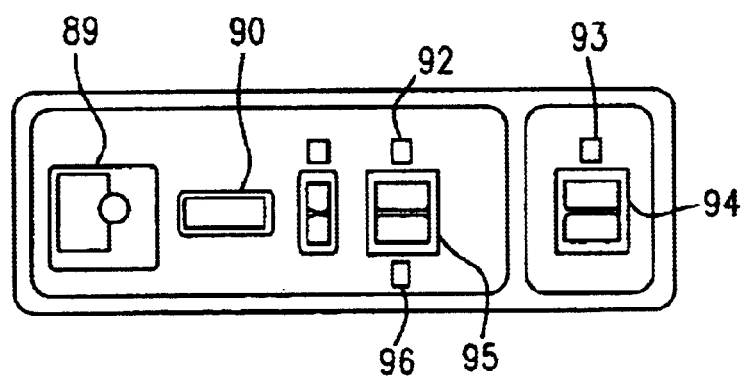

FIGS. 8A and 8B are illustrations of two schematic views of another embodiment the present invention violet/blue light source apparatus 100, wherein in FIG. 8A the apparatus 100 illumination source is installed within and operated from a single illumination head 81. The illumination head 81 is operated by a power supply and electronic control unit 87 and is supported by an adjustable height supporting mechanism 85. Lever 84 enables further fine adjustments of the lamp head 81 distance from the treated area, by sliding up or down and tightening at the requested position the support pole 83. Cable harness 82 connects the illumination head 81 to the power supply and electronic control unit 87. Control panel 86 enables the operation and control of the operational parameters of the power supply and electronic control unit 87. Unit 87 is supported by a set of four maneuvering wheels 88, having an integrated stop and fix in place mechanism.

FIG. 8B is a close look of control panel 86 in FIG. 8A. 89 is an electronic timing mechanism for controlling the treatment time. Counter 90 is a time-laps numerical indicator, for counting the accumulated operational hours of the illumination head 81. Switch 95 and indication lamps 92 and 96 enable switching and selecting the intensity of illumination between two discrete pre-selected energy levels. Switch 94 and the attached status indication lamp 93 is the system main power switch.

Figure 9A:
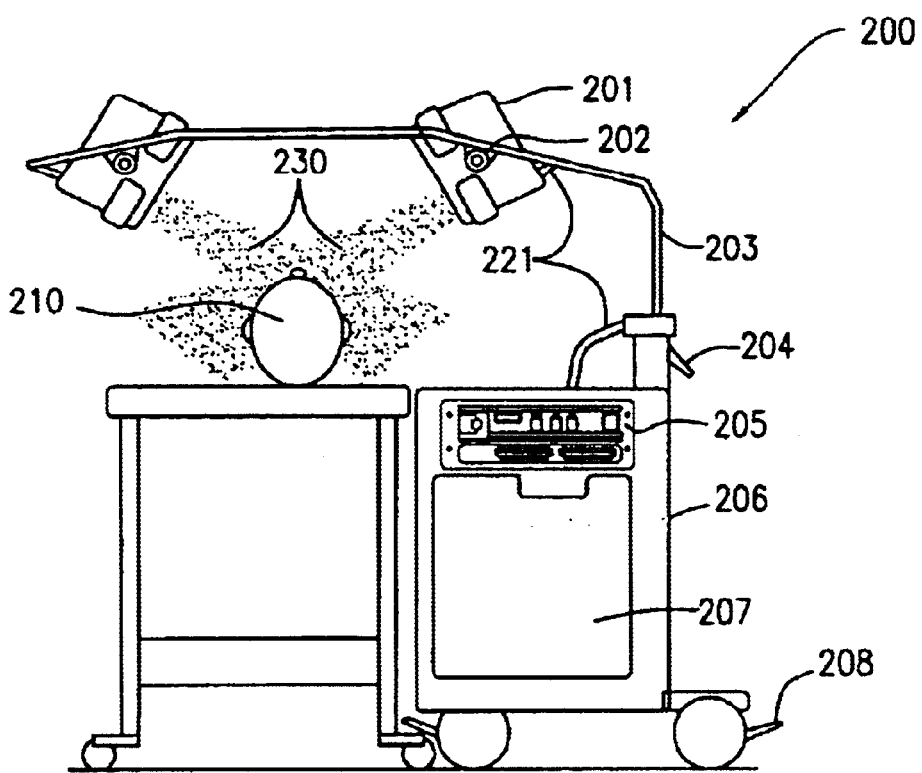
FIGS. 9A and 9B are two schematic views illustrations of another embodiment the present invention light source apparatus, wherein in FIG. 9A the illumination unit is structured of a dual illumination head configuration.
Figure 9B:
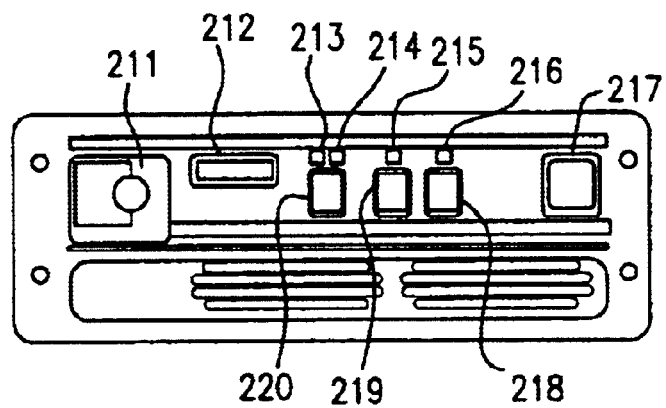

FIGS. 9A and 9B are two schematic views illustrations of another embodiment the present invention violet/blue light source apparatus 200, wherein in FIG. 9A the illumination source is structured of a dual illumination head module 201. The dual illumination head module 201 is operated by an integrated power supply and electronic control unit 206 and is supported by an adjustable height supporting mechanism 203. The head 210 height positioning, related to the treated area defined by the two illumination collimated light beams 230, is done by sliding up or down a supporting pole with an integrated piston unit which is a part of the support mechanism 203 and then tightening the lever 204 at the requested height. Gable harness 221 connects the illumination heads 201 to the power supply and electronic control unit 206. Control panel 205 enables the operation and control of the operational parameters of the power supply and electronic control unit 206. Unit 206 is supported by a set of four maneuvering wheels 208, having an integrated stop and lock mechanism. The two illumination heads can be slightly tilted by the operator around pivot axis 202, in order to adjust the positioning and consequentially the illumination energy distribution of the two illumination collimated light beams 230, to be equally and evenly distributed on the two face sides of the treated patient head 210.

FIG. 9B is a close look of control panel 205 in FIG. 9A. 211 is an electronic timing mechanism for controlling the treatment time. Counter 212 is a time-laps numerical indicator, for counting the accumulated operational hours of the dual beam illumination head module 201. Switch 220 and indication lamps 213 and 214 enable treatment duration control through timer 211 in one switch position, or unlimited operation time, by switching to the other switch position. Switch 219 and indication lamp 215 control the operation of a fan cooling module, integrated in the illumination head, having the task of cooling the slightly heated illuminated skin area of patient 210, during the treatment time. Switch 218 and indication lamps 216 enable switching and selecting the intensity of illumination between two discrete pre-selected energy levels. Switch 217 is the system self illuminated, main power switch.

Figure 10A:
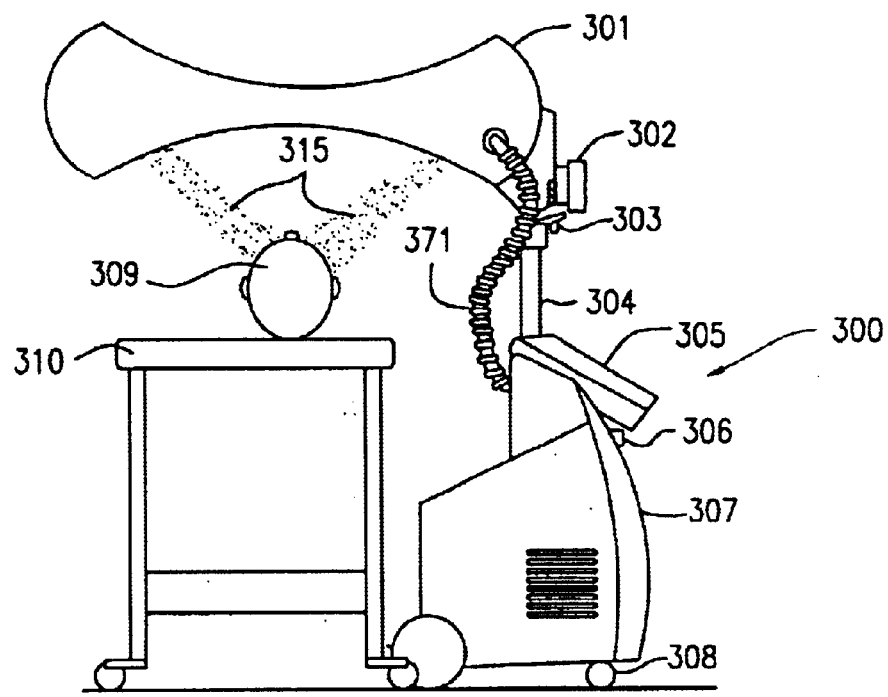
FIGS. 10A–10F, are schematic illustrations of another embodiment of the present invention light source apparatus, wherein the illumination head is structured of an integrated dual illumination source.

FIGS. 10A and 10–B, C and D are four schematic side views illustrations of another embodiment of the present invention violet/blue light source apparatus 300, wherein in FIG. 10A the illumination source is an integrated dual illumination source head 301. The dual illumination source head module 301 is operated by a power supply and electronic control unit 307 and is supported by an adjustable height, supporting mechanism 304. The adjustment of the lamp heads unit 301 distance from the treated area 310 and the patient treated skin area 309, is done by sliding up and down through the operation of an electro-mechanic piston to reach the requested position of the support pole 304. Cable harness 371 connects the illumination heads 301 to the power supply and electronic control unit 307. Digital videographic display control panel 305 enables the operation and control of all the operational parameters of the power supply, the electronic control and the computer modules of unit 307. Unit 307 is supported by a set of four maneuvering wheels 308, having an integrated stop and lock mechanism. The two illumination units inside the illumination head 301 can be slightly vertically tilted by the operator in order to adjust the positioning and consequently the illumination energy distribution of the two illumination collimated light beams 315, to be equally and evenly distributed on the two face sides of the treated patient 309.

Figures 10B, 10C, 10D:
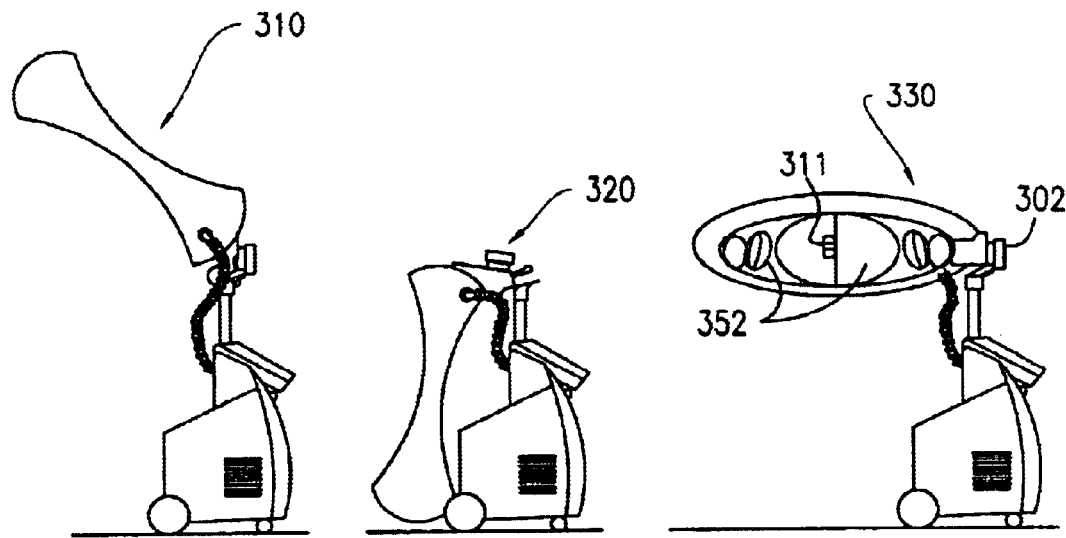

FIG. 10B, is the second of the four schematic side views of the present invention apparatus, showing another optional functional position of the illumination head, illustrating the present invention violet/blue light apparatus embodiment of FIG. 10A.

In FIG. 10B, the illumination head folding optional position 310 enables the up-tilting of the illumination head to a position required for temporary clinic storage periods and for the patient better maneuverability after treatment session completed to support post-treatment quick patient release requirements.

FIG. 10C is the illustration of the apparatus 300 in position 320, wherein the head is folded down to minimize size and packing volume for long term storage and for packaging and transportation.

In FIG. 10D, the illumination head of the apparatus 300 is pivoted around axis 302, thus enabling the head swivel to support in any requested "roll" angle position, this feature is desired to enable treating of a patient in a seated or partially-lying position. FIG. 10D also illustrates the integrated imaging module of the apparatus 300. Imaging sequence is first done is done by a miniature digital video and sill camera 311, installed in the center of the illumination source head 301. The acquisition step of the patient treated skin area picture by camera 311, is followed by the digital image processing, analysis and related treatment progress parameters evaluation by the apparatus 300 integrated computer module.

Figure 10E:
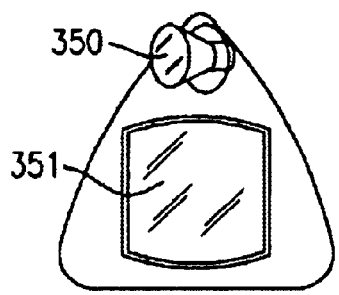
Figure 10F:
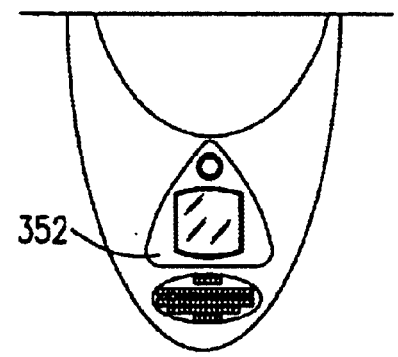

FIG. 10F is a look of illumination head 301 including the ventilation air input duct aperture 354 and illumination output-window aperture 352. FIG. 10E is a close look of the illumination output-window aperture 352 of the illumination head 301. Illumination output-window aperture 352 includes a halogen or tungsten filament lamp 350, geared for the illumination of the patient treated area, and an illumination unit glass protected output aperture window 351.

Figure 11A:
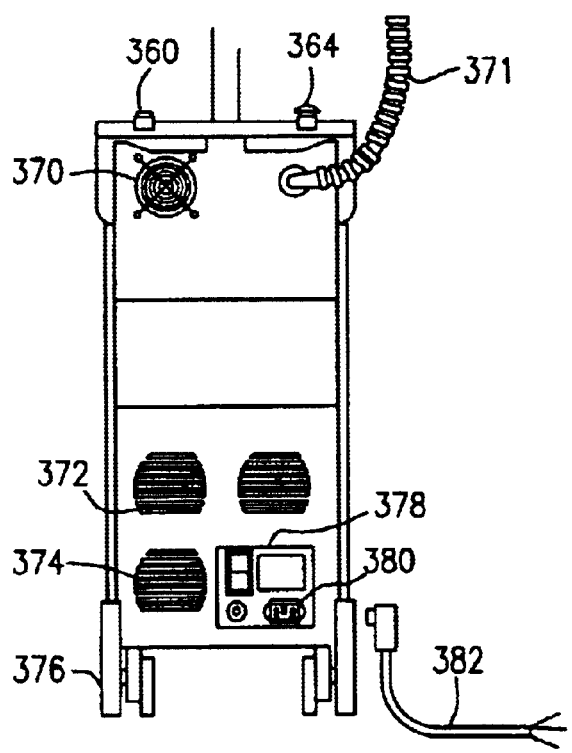
FIG. 11A is a back-side view of the present invention apparatus.
Figure 11B:
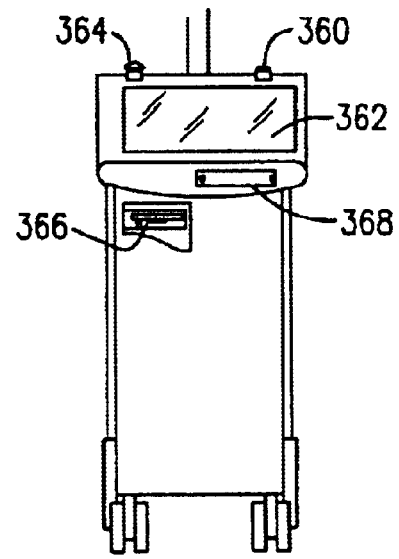
FIG. 11B is a close look of the computerized control panel in FIG. 10A.

FIG. 11B is a close look of the control panel 305 in FIG. 10A. 362 is a digital video-graphic display unit having preferably an overlaid touch screen unit that supports the registration and the X-Y positioning parameters of the operators touching point in any co-ordinate location on the screen. By touching the screen 362 on discrete points, when the treated skin area still image is displayed on the screen 362, the operator can electronically mark the affected areas, or points, on the treated skin area. The computer module of unit 307 can further accumulate the number and position information of the affected points and areas and further process this information to create and display on the apparatus screen 362 any required monitoring data regarding the healing effect progress from treatment to treatment. Switch 360 is the system main on-off switch that controls the system awakening and shutting-off processes through wire operating special commands on the system computer. 364 is a Panic switch that cuts-off the input power of the mains supply to the unit, in case of emergency. The computer module of unit 307 operates an adjustable electronic timing mechanism for controlling the treatment time. 306 is a Floppy diskette drive through which treatment data is downloaded from the system and back-up or revised software versions are uploaded to the apparatus 300 computer module.

FIG. 11A is a back-side view of system 300. 370 and 374 are ventilation units for the cooling of the computer and the electronic sub-units of the control unit 307. Switch 378 is the system main power/safety on-off circuit braker switch. 372 are two loudspeakers for generating computer synthetic voice commands and instructions to the system operator and the treated patient. Cable harness 371 is connecting and conducting the power lines and the control commands from the electronic and computer unit 307 to the illumination head 310. Cable 382 is the mains supply cable and plug and 380 is the power input socket.

In Vitro Experimentation

Bacterial strain—The strain used in this study was *Propionibacterium acnes* 6919 which was obtained from the American Type Culture Collection (ATCC) at Rockville, Md. U.S.A.

Growth media—*Propionibacterium acnes* was grown on Reinforced Clostridial Agar from Oxoid (Basingstoke, Hampshire England) at pH =6–6.2.

Illumination tests were carried out when bacteria were grown in Reinforced Clostridial Broth which was prepared from the same ingredients except the agar at pH 6–6.2.

Illumination method—Illumination was carried out by CureLight's acne therapy system. Under blue light at the wavelength of 407 nm Illumination periods were 15 minutes, 30 minutes or 60 minutes as indicated in the text. Lamp intensity was 20 mW/cm$^2$.

Bacterial growth and illumination—*Propionibacterium acnes* was transferred from the bacterial stock into Reinforced Clostridial Agar Plates. Bacteria were streaked on the plates for isolation of single colonies by the "clock plate technique". These plates were called "Start plates" and were incubated for three days under aerobic conditions in an anaerobic jar. The jar contained Aaero Gen sachets from Oxoid, England to maintain anaerobic conditions suitable for *P. acnes*.

From the "start plates" single colonies were transferred into Reinforced Clostridial Broth and allowed to grow anaerobiclly for 24 hours or for 72 hours. Bacteria grown for 24 hours were defined as "young culture" and those grown for 72 hours were defined as "old culture". The "young" or the "old" cultures were transferred to illumination for the indicated times. Some cultures were illuminated again after 24 hours or 48 hours from the first illumination as indicated in the results. After each illumination a sample was taken out from the culture and viable bacteria were counted. Viable bacteria were monitored and calculated by counting the colony forming units after appropriate dilution in saline and cultivation on the Reinforced Clostridial Agar plates under anaerobic conditions for three days. The colony forming units of the survivals were calculated per ml. Untreated cultures served as controls.

Figure 7:
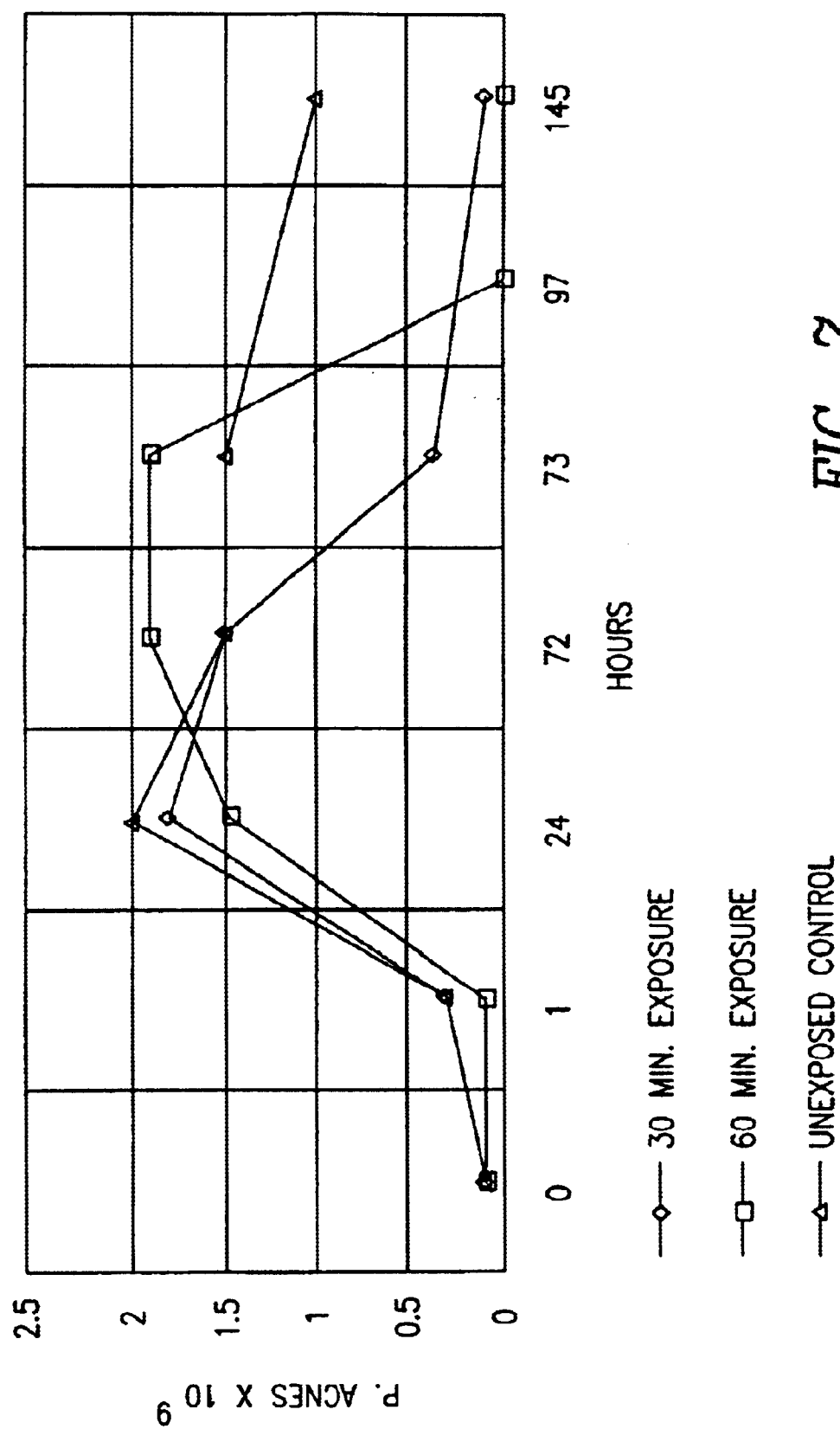
FIG. 7 illustrates the results of the proposed apparatus, operated under laboratory controlled tests on *p. acne*, showing a decrease in *propionibacterium acnes* in 4–5 orders of magnitude, after two 30, or 60 minutes exposures separated by 72 hours of dark incubation.

Results have shown that exposure to the proposed apparatus achieves a decrease in *propionibacterium acnes* from 109 to <104 after two 30, 60 minutes exposures separated by 72 hours of dark incubation, as shown in FIG. 7.

In addition, the destruction of *p. acnes* may be further enhanced by adding methylene blue 0.5% to the broth prior to irradiation.

Extensive pre-clinical tests were performed at Bar-Ilan University—Natural sciences lab by Prof. Zvi Malik and Prof. Yashayahu Nitzan.

Results:

Illumination of "young" cultures—*Propionibacterium acnes* which was grown on a "start plate" was transferred into Reinforced clostridial Broth and incubated for 24 hours. After this period two illumination courses of 30' minutes each were carried out in an interval of 48 hours from the first to the second illumination. The results demonstrate a decrease of 1 order of magnitude in viability of the culture in comparison to the control. When the culture taken from the "start plate" was grown for 24 hours and illuminated twice, this time for 60 minutes each and 48 interval between the illuminations, two orders of magnitude decrease in viability were demonstrated.

Illumination of "old cultures"—*Propionibacterium acnes* which was grown on a "start plate" was transferred into Reinforced Clostridial Broth and incubated for 72 hours. Bacterial cultures were illuminated once for 15 minutes or once for 60 minutes. Illumination in both illumination periods resulted in a decrease in the cultures viability of one order of magnitude. In addition, illumination of the old culture for two times and 30 minutes in an interval of 24 hours resulted in the decrease in viability of two orders of magnitude. When the "old" culture is illuminated twice for 60 minutes at an interval of 24 hours a decrease of four orders of magnitude is demonstrated in their viability.

Figure 12:
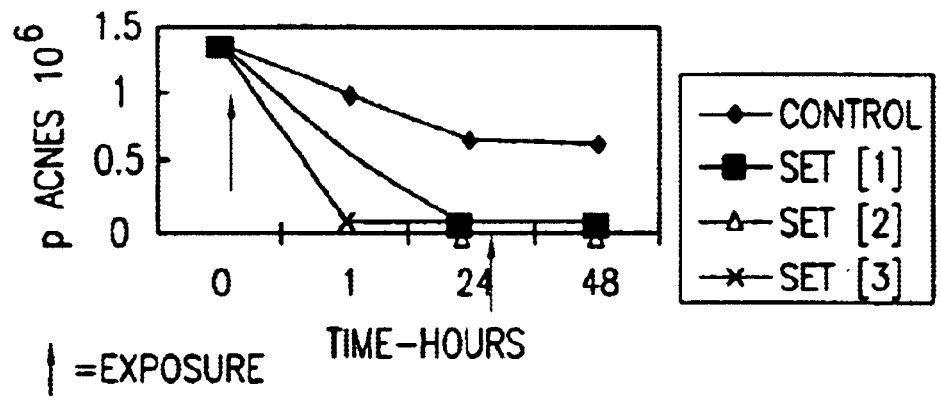
FIGS. 12 & 13 are graphical illustrations of the treatment of *p.acnes* using the apparatus of FIG. 1.
Figure 13:
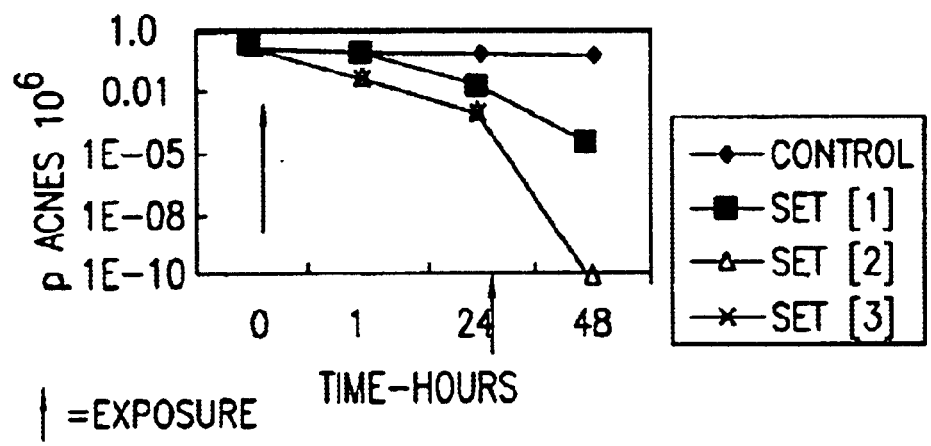

As shown in FIGS. 12 and 13, significant destruction of *p. acnes* was achieved up to 4 orders of magnitude.

In Vivo testing

Topical formulations were investigated in the Hyperbaric Chamber unit Elisha Hospital in Haifa.

Figure 14:
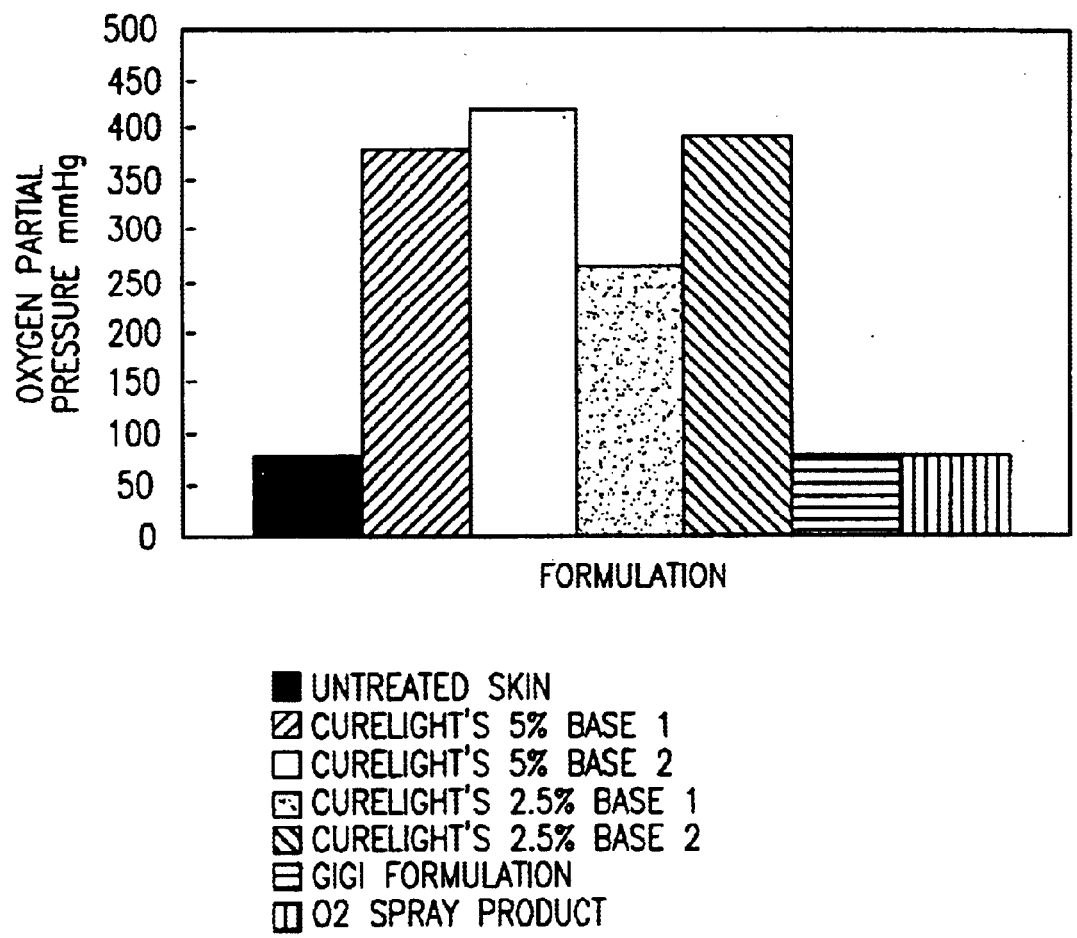
FIG. 14 is a graphical illustration of the oxygen enhancement using different formulations for the treatment of *p.acnes*.

Tco$_2$M transcutaneous Co$_2$/o$_2$ Monitor Model 860 by Novametrix Medical Systems was used to measure cutaneous oxygen. Transcutaneous oxygen was measured with an oxygen sensor consisting of 2 parts; [1] A modified Clark type polarographic electrode, a silver anode and platinum cathode, electrolyte and a oxygen permeable membrane [2] a heating section with two precision thermistors for measuring and controlling the sensor temperature. Results, shown in FIG. 14, are as follows.

| | |
|---|---|
| Control measurement (nothing applied) | 77 mmHg |
| Invented formulation 5% base I (prepared 5/99) | 380 mmHg |
| Invented formulation 5% base II (prepared 5/99) | 430 mmHg |
| Invented formulation 2.5% base I (prepared 1/99) | 270 mmHg |
| Invented formulation .5% base I (prepared 1/99) | 400 mmHg |
| Other "Oxygen enhancing" commercial formulation | 75 mmHg |
| O2 Spray Product | 75 mmHg |

Formulations are steady for at least 4 months.

It is to be understood that the invention is not limited in its applications to the details of construction or drawings. The invention is capable of other embodiments, or of being practiced or carried out in various ways, Also, it is to be understood that the phraseology and terminology employed above is for the purpose of description and should not be regarded as limiting. While the invention has been described with respect to a limited number of embodiments, it will be appreciated that many variations, modifications and other applications of the invention may be made.

While the invention has been described with respect to a limited number of embodiments, it will be appreciated that many variations, modifications and other applications of the invention may be made.

What is claimed is:

1. Apparatus for the treatment of a treatment area exhibiting a skin disorder and associated inflammation lying at or near the surface of the skin of a patient comprising:
   (a) a self supporting mechanical fixture for holding at least one light source in a fixed position spaced apart from the treatment area during treatment thereof, said mechanical fixture comprising securing means for operatively securing the light source to the fixture and adjustment means for adjusting the distance or position of the light source from the treatment area;
   (b) at least one light source for emitting light with a peak spectral emittance concentrated in at least one narrow spectral band with the peak spectral emittance in one of said narrow spectral bands being in the range of 405 to 440 nm with an illumination power at the treatment area of 10 to 500 mw/cm$^2$, said securing means of the mechanical fixture securing the light source in said fixed position when the light source is emitting the light;
   (c) an optical system for collecting and shaping the spectral emittance in advance of delivering the spectral emittance to the treatment area; and
   (d) electronic means for controlling parameters associated with the spectral emittance.

2. The apparatus of claim 1 comprising an illumination head comprising at least two converging collimated beams from at least two directions, each of said beams generated by a separate light source positioned at a distance from said other at least one light source.

3. The apparatus of claim 1 wherein the at least one light source is an ion krypton gas laser light source.

4. The apparatus of claim 1 wherein the system for shaping and collecting the spectral emittance is an optical system comprising two orthogonal cylindrical lenses.

5. The apparatus of claim 1 wherein each of the spectral bands is a narrow spectral band.

6. The apparatus of claim 1 further comprising cooling means for removing excess heat from the treatment area of the skin disorder.

7. The apparatus of claim 1 wherein the spectral emittance means comprises means for delivering a dose of at least 18 Joules/cm$^2$.

8. The apparatus of claim 1 wherein the spectral emittance means comprises means for delivering a dose of at least 36 Joules/cm$^2$.

9. The apparatus of claim 1 wherein the light source emits UV radiation, said apparatus further comprising filtering means for removing at least substantially all of the UV radiation emitted by the light source.

10. The apparatus of claim 1 wherein said light source delivers a principal skin disorder treating effective spectral emittance of light energy range in the range of 405 to 450 nm.

11. The apparatus of claim 1, wherein said parameters are selected from the group consisting of duration, radiated power and emitted spectral bands of said spectral emittance.

12. The apparatus of claim 1 wherein the treatment area is the head of a patient including a face and a chin, said light source comprising means for delivering the spectral emittance of energy to the face, the chin or combination thereof.

13. The apparatus of claim 1, wherein said spectral emittance has a power density of at least 20 mW/cm$^2$.

14. The apparatus of claim 1 wherein said spectral emittance has a power density of at least 40 mW/cm$^2$.

15. The apparatus of claim 1 comprising means for delivering the spectral emittance for a minimum treatment time of 15 minutes.

16. The apparatus of claim 15 comprising means for delivering the spectral emittance for a treatment time of from 15 to 60 minutes.

17. The apparatus of claim 1 wherein the adjustment means adjusts the distance or position of the light source to enable treatment of a treatment area of at least 200 cm$^2$.

18. The apparatus of claim 1, wherein the optical system further comprises:
   at least one optical element selected from the group consisting of a liquid filled light guide, a solid transparent light guide, a fiber bundle light guide and an array of lenses and mirrors for collecting and shaping said spectral emittance and for illuminating a treatment area at an adjustable distance, energy density and direction.

19. The apparatus of claim 1, wherein said at least one light source is a gas discharge lamp.

20. The apparatus of claim 1, wherein said at least one light source comprises at least one material selected from the group consisting of Gallium, Mercury and metal halides in the form of a gas mixture discharge lamp.

21. The apparatus of claim 1, wherein said at least one light source further comprises at least one reflector for collecting and projecting the spectral emittance toward the skin disorder.

22. The apparatus of claim 21 wherein said reflector is selected from the group comprising of an elliptical cross-section cylindrical reflector, a parabolic cross-section cylindrical reflector, and an asymmetric aspheric reflector.

23. The apparatus of claim 1, wherein the electronic means for controlling parameters associated with the spectral emittance comprises an integrated computer module.

24. The apparatus of claim 1, wherein said at least one light source is at least one diode selected from the group consisting of violet/blue laser diodes and light emitting diodes (LED), and combinations thereof with a narrow spectral band emission in the range 405–440 nm.

25. The apparatus of claim 1, wherein said at least one light source is an array of diodes selected from the group consisting of violet/blue light emitting diodes (LED) and laser diodes, and red and green light emitting diodes (LED) and laser diodes.

26. The apparatus of claim 1, wherein said at least one light source is selected from the group consisting of LED diodes, laser diodes and gas discharge lamps and combinations thereof.

27. The apparatus of claim 1, wherein the spectral emittance of at least one spectral band is in the green and red range.

28. The apparatus of claim 1 wherein the skin disorder is selected from the group consisting of acne and seborrhea.

29. A method of treating a treatment area exhibiting a skin disorder and associated inflammation at or near the surface of the skin of a patient comprising:

(a) positioning in an operative treating position for treating a skin disorder a self supporting mechanical fixture comprising at least one light source in a fixed position spaced apart from the treatment area, said mechanical fixture comprising securing means for operatively securing the light source to the fixture, and adjustment means for adjusting the distance or position of the light source from the treatment area; and (b) applying to the treatment area in a plurality of discontinuous applications a peak spectral emittance of light energy at least in the substantial absence of UV radiation sufficient to effectively treat the skin disorder, said peak spectral emittance concentrated in at least one narrow spectral band with the peak spectral emittance of one of said narrow spectral bands being in the range of 405 to 440 nm with an illumination power at the treatment area of 10 to 500 mw/cm$^2$ while maintaining the treatment area at a patient acceptable temperature.

30. The method of claim 29 wherein the skin disorder is caused by skin disorder generating bacteria, said method comprising applying said spectral emittance of light energy for a time sufficient to facilitate the reaction of porphoryins produced by the bacteria and oxygen to produce peroxides which are toxic to the bacteria.

31. The method of claim 29 comprising applying said spectral emittance of light energy at time periods which enable the porphoryins produced by the bacteria during the time period between each application to react with oxygen in the presence of said spectral emittance and consequently to produce peroxides and for the peroxides to kill the bacteria in sufficient amounts so as to reduce the mass of bacteria associated with the skin disorder, and repeating the application until the bacteria mass is reduced below a predetermined level.

32. The method of claim 29 further comprising removing heat from the skin to maintain the skin at a patient acceptable temperature.

33. The method of claim 29 comprising applying to the treatment area a spectral emittance of light energy which has had UV radiation filtered therefrom.

34. The method of claim 29 wherein each discontinuous application is at least 15 minutes.

35. The method of claim 29 wherein each discontinuous application is from 15 to 60 minutes.

36. The method of claim 29 wherein the treatment area of the skin disorder is at least 200 cm$^2$.

37. The method of claim 29 comprising controlling parameters associated with the spectral emittance of light energy through an integrated computer module.

38. The method of claim 37 wherein the integrated computer module comprises a display unit for displaying an imaged illumination treatment area.

39. The method of claim 38 wherein the integrated computer module comprises a display unit comprising a touch screen.

40. The method of claim 29, wherein the spectral emittance of light energy is from at least one diode selected from the group consisting of violet/blue laser diodes and light emitting diodes (LED), and combinations thereof with narrow spectral band emission in the range 405–440 nm.

41. The method of claim 29, wherein the spectral emittance of light energy is from an array of diodes selected from the group consisting of violet/blue light emitting diodes (LED) and laser diodes, and light emitting diodes (LED) and laser diodes with spectral bands emission in the red and green range.

42. The method of claim 29, wherein the spectral emittance of light energy is from a member selected from the group consisting of LED diodes, laser diodes and gas discharge lamps and combinations thereof.

43. The method of claim 29, wherein the spectral bands of the spectral emittance are in the violet/blue range and at least one spectral band in the green and red range.

44. The method of claim 29 wherein the skin disorder is selected from the group consisting of acne and seborrhea.

* * * * *